(12) United States Patent
Joe Anto et al.

(10) Patent No.: US 11,110,298 B2
(45) Date of Patent: Sep. 7, 2021

(54) INTENSITY MODULATED PROTON THERAPY (IMPT) PLAN OPTIMIZATION BASED AT LEAST ON INTERNAL ORGAN ANTICIPATED MOVEMENT AND/OR EXPECTED DEFORMATION

(71) Applicant: KONINKLIJKE PHILIPS N.V., Eindhoven (NL)

(72) Inventors: Gipson Joe Anto, Kaliyal (IN); Vaitheeswaran Ranganathan, Bangalore (IN); Ajesh Kumar, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 595 days.

(21) Appl. No.: 16/061,443

(22) PCT Filed: Dec. 12, 2016

(86) PCT No.: PCT/IB2016/057523
§ 371 (c)(1),
(2) Date: Jun. 12, 2018

(87) PCT Pub. No.: WO2017/109632
PCT Pub. Date: Jun. 29, 2017

(65) Prior Publication Data
US 2020/0261743 A1    Aug. 20, 2020

Related U.S. Application Data

(60) Provisional application No. 62/270,616, filed on Dec. 22, 2015.

(51) Int. Cl.
*A61N 5/10* (2006.01)

(52) U.S. Cl.
CPC .......... *A61N 5/1037* (2013.01); *A61N 5/1031* (2013.01); *A61N 5/1039* (2013.01);
(Continued)

(58) Field of Classification Search
CPC .......... A61N 5/1031; A61N 2005/1087; A61N 5/1037; A61N 5/1039; A61N 2005/1074; A61N 5/1045
See application file for complete search history.

(56) References Cited

U.S. PATENT DOCUMENTS

| | | | |
|---|---|---|---|
| 8,433,159 B1 | 4/2013 | Nord | |
| 8,644,571 B1 * | 2/2014 | Schulte | A61N 5/1077 382/128 |

(Continued)

FOREIGN PATENT DOCUMENTS

| | | |
|---|---|---|
| EP | 2759317 | 7/2014 |
| WO | 2009016530 | 2/2009 |
| WO | 2016/070938 | 5/2016 |

OTHER PUBLICATIONS

Heath, et al., "Incorporating uncertainties in respiratory motion into 4D treatment plan optimization" Medical Physics, vol. 36, No. 7, Jun. 11, 2009.

(Continued)

*Primary Examiner* — Christine H Matthews
*Assistant Examiner* — Joshua Daryl D Lannu

(57) ABSTRACT

A method includes generating a nominal dose distribution based on an image and clinical goals. The method further includes generating a setup error dose distribution based on range and setup uncertainties. The method further includes generating a dose distribution for a parameter of an internal organ. The method further includes optimizing a planned dose distribution of an intensity modulated proton therapy plan by minimizing a total objective value including the nominal dose distribution, the setup error dose distribution dose distribution, and the dose distribution for the internal (Continued)

organ. The method further includes generating a final dose distribution for the intensity modulated proton therapy plan based on beam parameters of the optimized planned dose distribution. The method further includes controlling a proton therapy apparatus configured to deliver proton therapy based on the intensity modulated proton therapy plan with the optimized planned dose distribution.

21 Claims, 6 Drawing Sheets

(52) U.S. Cl.
CPC .... *A61N 5/1045* (2013.01); *A61N 2005/1074* (2013.01); *A61N 2005/1087* (2013.01)

(56) References Cited

U.S. PATENT DOCUMENTS

2004/0254773 A1* 12/2004 Zhang ................. A61B 6/541
  703/11
2014/0226884 A1   8/2014 Porikli

OTHER PUBLICATIONS

Goitein, "Calculation of uncertainty in the dose delivered during radiation therapy," Med. Phys. 12, 608-612 (1985).

Unkelbach et al., "Accounting for range uncertainties in the optimization of intensity modulated proton therapy", Phys. Med. Biol. 52 (2007) 2755-2773 (2007).

Unkelbach et al. "Reducing the sensitivity of IMPT treatment plans to setup errors and range uncertainties via probabilistic treatment planning" American Association of Physicists in Medicine (2009).

Kohler et al., "MR-only simulation for radiotherapy planning", White paper: Philips MRCAT for prostate dose calculations using only MRI data, 2016.

David Spagnoli, "Innovations—prostate cancer; MR-only simulation for prostate RT planning*" http://www.philips.com.eg/healthcare/education-resources/publications/hotspot/prostate-rt-planning.

* cited by examiner

| 300 | 304 ROI | 312 AP | 314 SI | 316 ML |
|---|---|---|---|---|
| 302 RECTUM | 306 0.6 | 308 0.8 | 310 0.4 |
FIGURE 3
| 400 | 404 ROI | 412 AP | 414 SI | 416 ML |
|---|---|---|---|---|
| 402 BLADDER | 406 1.0 CM | 408 0.5 CM | 410 -1.2 CM |
FIGURE 4
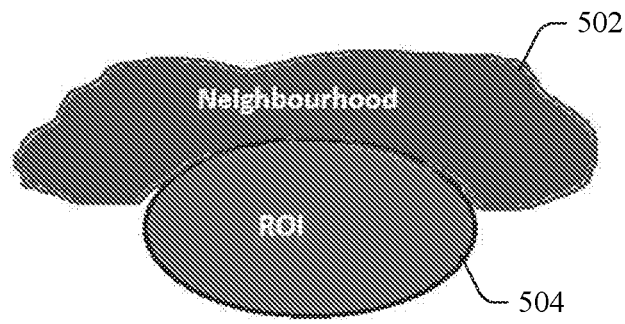
FIGURE 5
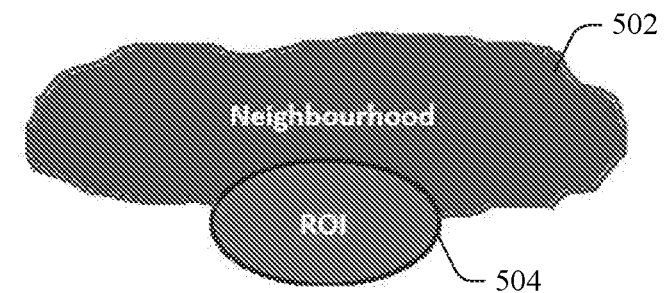
FIGURE 6

INTENSITY MODULATED PROTON THERAPY (IMPT) PLAN OPTIMIZATION BASED AT LEAST ON INTERNAL ORGAN ANTICIPATED MOVEMENT AND/OR EXPECTED DEFORMATION

CROSS REFERENCE TO RELATED APPLICATIONS

This application is the U.S. National Phase application under 35 U.S.C. § 371 of International Application No. PCT/IB2016/057523, filed Dec. 12, 2016, published as WO 2017/109632 on Jun. 29, 2017, which claims the benefit of U.S. Provisional Patent Application No. 62/270,616 filed Dec. 22, 2015. These applications are hereby incorporated by reference herein.

FIELD OF THE INVENTION

The following generally relates intensity modulated proton therapy (IMPT), and more particularly to optimizing an IMPT plan based at least on internal organ anticipated movement and/or expected deformation.

BACKGROUND OF THE INVENTION

Intensity modulated proton therapy (IMPT) uses a beam of protons to irradiate diseased tissue, e.g., in the treatment of cancer. Failing to account for errors such as range and setup uncertainties in the IMPT plan may result in a delivered dose distribution that is inferior to the planned dose distribution. Range uncertainty corresponds to the uncertainty of the location of the Bragg peak with respect to anatomical structures (i.e., the range of a proton beam in the patient). This uncertainty can be from the uncertainty in CT Hounsfield units and the conversion to stopping power, artifacts in the CT image, and geometric changes of the patient. Setup uncertainty is due to a positional shift of the patient, which may cause misalignment of dose contributions from different beam directions and misalignment of density heterogeneities.

Robust Optimization (RO) is a technique for optimizing an IMPT plan. RO has been used to optimize an IMPT plan by taking into account setup error. Setup uncertainty can be modeled by simulating a set of independent uncertainty cases that mimic whole body movement of the patient in six directions (three pair of positive and negative coordinates). For range and setup error, the RO minimizes a total objective value (RO OBV), which includes a clinical objective component (Nominal Plan OBV) and a patient setup error component (Setup Error OBV). EQUATION 1 provides an example of such an optimization.

RO(Setup error) OBV=Nominal Plan OBV+Setup Error OBV,   EQUATION 1:

where Set up error OBV=(+X error OB)+(−X error OBV)+(+Y error OBV)+(−Y error OBV)+(+Z error OBV)+(−Z error OBV)+(Range undershoot error OBV)+(Range overshoot error OBV). Each objective value represents a respective uncertainty scenario. For example, +X error OBV is the objective value obtained from the dose statistics when the patient is shifted in a positive X direction by a factor specified by the user.

Non-limiting examples of determining error and IMPT planning are described in Goitein, "Calculation of uncertainty in the dose delivered during radiation therapy," Med. Phys. 12, 608-612 (1985), Unkelbach et al., "Accounting for range uncertainties in the optimization of intensity modulated proton therapy, Phys. Med. Biol. 52 (2007) 2755-2773 (2007), and Unkelbach et al. "Reducing the sensitivity of IMPT treatment plans to setup errors and range uncertainties via probabilistic treatment planning" American Association of Physicists in Medicine (2009).

EQUATION 1 is well-suited for setup errors such as whole body patient movement, e.g., three millimeters (3 mm) with the modern immobilization devices. However, EQUATION 1 does not take into account internal organ movement and/or deformation, such as in the case of the bladder or rectum, which tends to be of a large magnitude relative to setup errors, and the probability of occurrence for this error tends to increase over time. Unfortunately, such movement and/or deformation may result in a wrong dose due to a positional change with respect to beams.

SUMMARY OF THE INVENTION

Aspects described herein address the above-referenced problems and/or others.

In one aspect, a method includes generating a nominal dose distribution based on an image and clinical goals. The method further includes generating a setup error dose distribution based on range and setup uncertainties. The method further includes generating a dose distribution for a parameter of an internal organ. The method further includes optimizing a planned dose distribution of an intensity modulated proton therapy plan by minimizing a total objective value including the nominal dose distribution, the setup error dose distribution dose distribution, and the dose distribution for the internal organ. The method further includes generating a final dose distribution for the intensity modulated proton therapy plan based on beam parameters of the optimized planned dose distribution. The method further includes controlling a proton therapy apparatus configured to deliver proton therapy based on the intensity modulated proton therapy plan with the optimized planned dose distribution.

In another aspect, a system includes a proton therapy apparatus configured to deliver proton therapy and a controller configured to control the proton therapy apparatus. The system further includes a treatment planner configured to generate an optimized intensity modulated proton therapy plan based on an input image, a nominal dose distribution, a setup error dose distribution, and a dose distribution for at least one of an internal organ movement or an internal organ deformation. The system further includes a console (122) configured to instruct the controller to control the proton therapy apparatus to transmit a proton beam based on the optimized intensity modulated proton therapy plan.

In another aspect, a non-transitory computer readable medium is encoded with computer executable instructions, which when executed by a processor, causes the processor to: receive an image, receive a first input indicative of a nominal dose distribution for the image and clinical goals, receive a second input indicative of a whole body dose distribution for range and setup uncertainties, receive a third input indicative of an anticipated movement of an internal organ, receive a fourth input indicative of an expected deformation of the internal organ, warp the image based on the anticipated movement and the expected deformation, generating a warped image, compute a dose distribution for the warped image, optimize a planned dose distribution of an intensity modulated proton therapy based on the nominal dose distribution, the whole body movement distribution and the dose distribution for the anticipated movement and the expected deformation, export beam parameters obtained from the optimization to the received image, and generate a final dose distribution for the intensity modulated proton therapy plan based the beam parameters.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 3 schematically illustrates a GUI for entering anticipated organ movement in three-dimensions.

FIG. 4 schematically illustrates a GUI for entering expected organ deformation in three-dimensions.

FIG. 5 schematically illustrates a simple elastic expansion-contraction mode for neighborhood density-warping where a neighborhood region contracts when an ROI expands;

FIG. 6 schematically illustrates the simple elastic expansion-contraction mode where the neighborhood region expands when the ROI contracts;

DETAILED DESCRIPTION OF EMBODIMENTS

Figure 1:
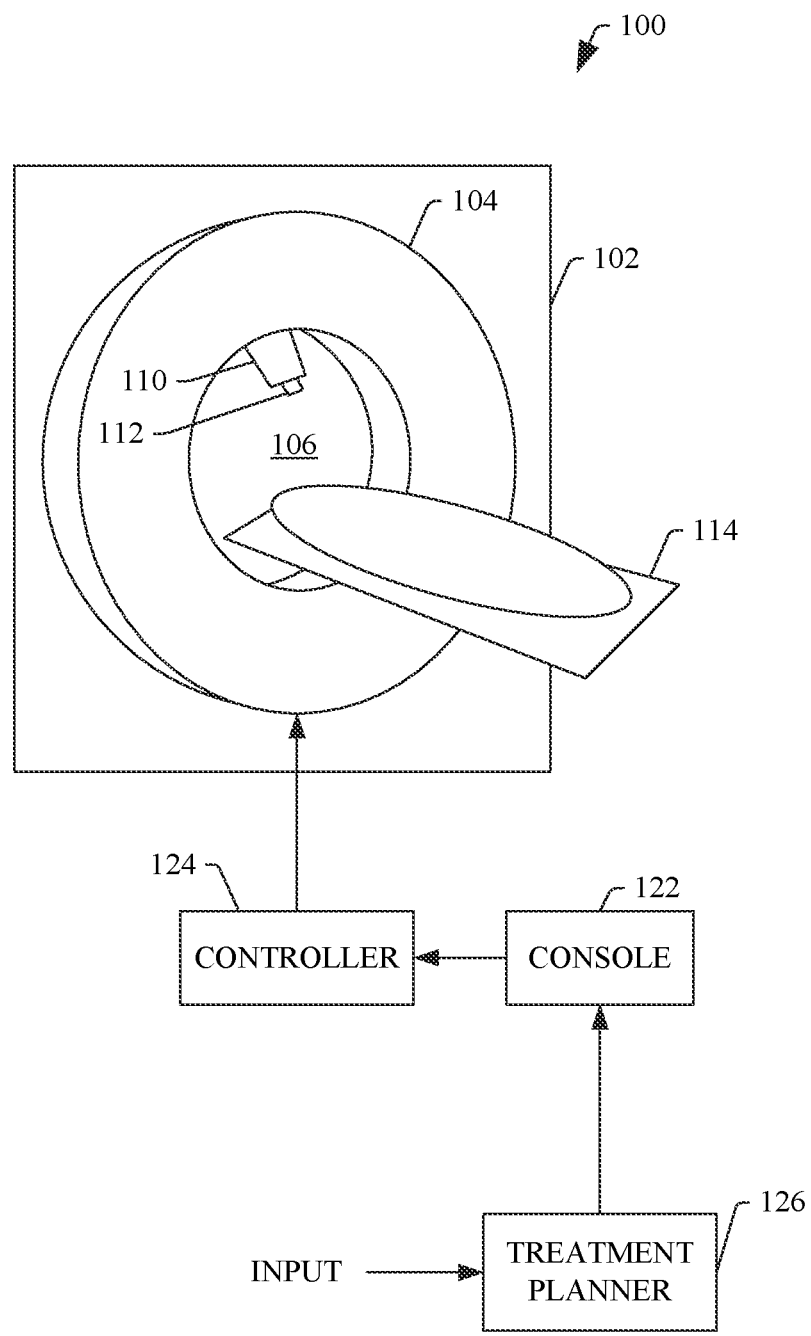
FIG. 1 schematically an example therapy system configured for Intensity modulated proton therapy (IMPT).

FIG. 1 schematically illustrates a therapy system 100 configured for intensity modulated proton therapy (IMPT.

A stationary gantry 102 rotatably supports a rotating gantry 104, which rotates with respect to a rotation axis about a treatment region 106. A nozzle 110 houses beam modifying components and delivers the proton beam. A snout 112 supports the aperture and compensator. A support 114 supports a portion of a subject in the treatment region 106. A proton source, such as a 70 MeV proton accelerator, produces a proton beam.

An operator console 122 includes human readable output devices such as a display monitor and input devices such as a keyboard and/or mouse. Software accessible on and executable by a processor of the console 122 allows the operator to control an operation of the therapy system 100. A controller 124 is configured to control rotation of the rotating gantry 104 and the subject support 116 and delivery of treatment protons by the proton source during a treatment.

A treatment planner 126 creates IMPT treatment plans. As described in greater detail below, in one instance the treatment planner 126 is configured to optimize IMPT treatment plans based at least on internal organ movement and/or deformation. For example, in one instance the treatment planner 126 is configured to optimize IMPT treatment plans based on set up error and internal organ movement and/or deformation. In other embodiments, the treatment planner 126 is configured to optimize IMPT treatment plans based on more or less, additional or different, etc. features.

It is to be appreciated that the treatment planner 126 can be implemented via one or more processors (e.g., micro-processor, central processing unit, controller, etc.) executing one or more computer readable instructions. In one instance, the one or more computer readable instructions are encoded on non-transitory computer readable storage medium such a physical memory and/or other non-transitory medium. Additionally or alternatively, at least one of the computer readable instructions can be carried by a carrier waver, a signal and/or other transitory medium.

Figure 2:
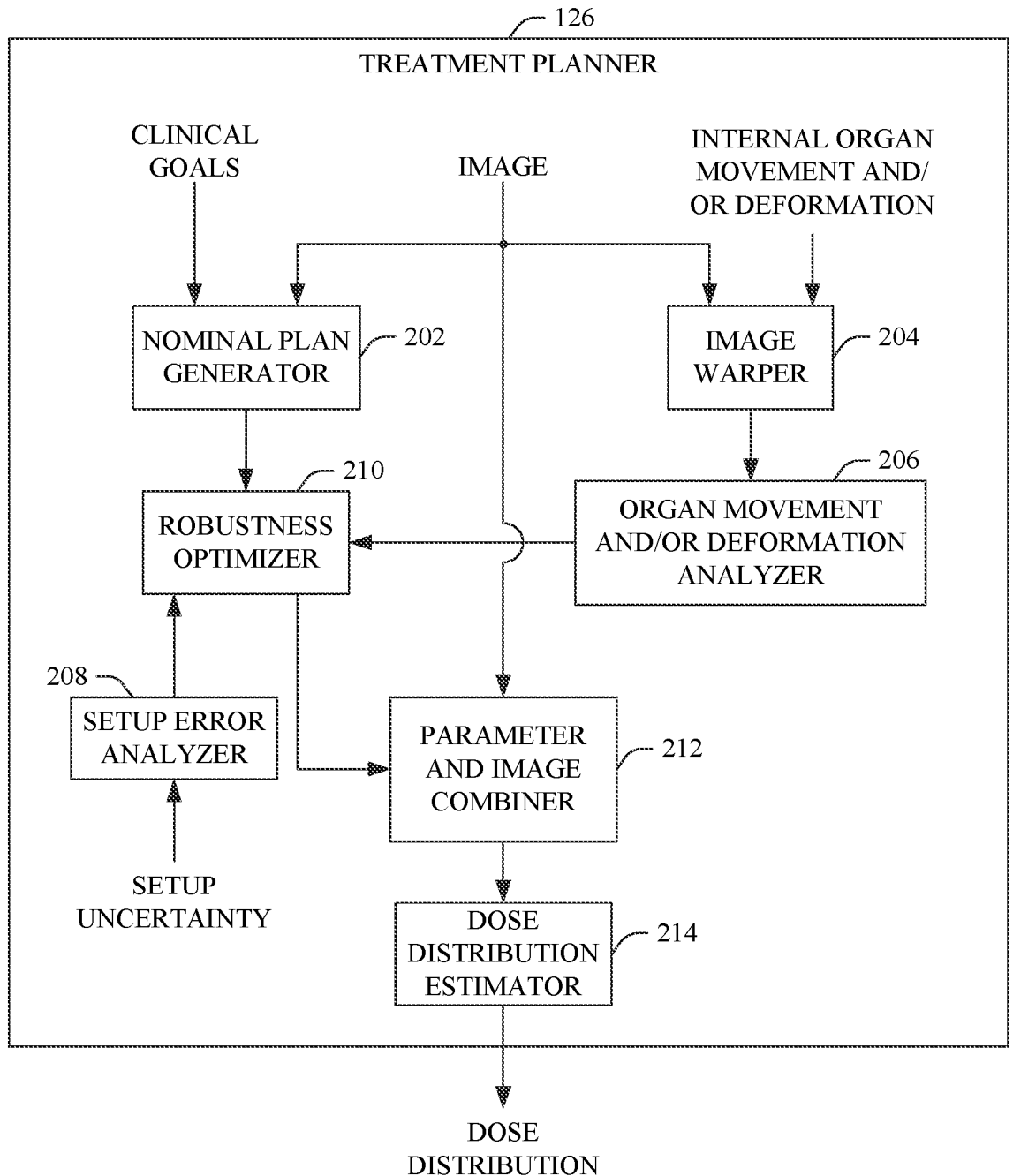
FIG. 2 schematically illustrates an example of the treatment planner of the therapy system.

FIG. 2 illustrates a non-limiting example of the treatment planner 126.

The treatment planner 126 receives, as input, an image and clinical (user specified) goals. The image can be a computed tomography (CT), magnetic resonance (MR), positron emission tomography (PET), and/or other modality image. The image can be received from an imaging system, a data repository (e.g., picture archiving and communication system (PACS), a radiology information system (RIS), etc.), local memory, etc. Examples of clinical goals include a specific machine parameter setting (e.g., number of spots, spot monitor unit (MU), etc.), dose-volume histogram (DVH), dose distribution and a Composite Objective Value. A nominal plan generator 202 is configured to generate an optimized nominal IMPT plan based on the image and the clinical goals. The nominal plan includes an estimated nominal dose distribution, e.g., dose statistics of each region of interest (ROI).

The treatment planner 126 further receives, as input, anticipated ROI movement in one or more dimensions and/or an expected worst case of deformation for the ROI. Briefly turning to FIGS. 3 and 4, example graphical user interfaces (GUIs) 300 and 400 for entering organ movement and organ deformation in three-dimensions are illustrated. From FIG. 3, the GUI 300 includes a first field 302 for selecting a ROI 304 from a pre-determined list, and fields 306, 308 and 310 for entering expected organ movement along Antero-posterior (AP) 312, Superior-inferior (SI) 314 and Medio-Lateral (ML) 316 directions. From FIG. 4, the GUI 400 includes a first field 402 for selecting a ROI 404, and fields 406, 408 and 410 for entering a range of deformation along AP 412, SI 414 and ML 416 directions. In a variation, a location and/or a size/shape of the/ROI can be entered and/or edited.

Returning to FIG. 2, an image warper 204 warps the input image based on the anticipated ROI movement and/or the expected ROI deformation, producing a warped image or model. For this, the input is converted to a set of deformation vector fields (DVFs), which is applied on an external contour of the ROI to warp the ROI (ROI-warping), the region of the image contained within the ROI (ROI density-warping) and/or regions in a predetermined vicinity about the deformed ROI (neighborhood density-warping). This will produce warping inside the ROI as well as in the regions adjacent to the ROI. In one instance, the neighborhood density-warping is done by assuming a simple elastic expansion-contraction model. In this approach, as shown in FIG. 5, a neighborhood region 500 contracts if an ROI 504 expands, and, as shown in FIG. 6, the neighborhood region 500 expands if the ROI 502 contracts.

The elastic model for neighborhood-density warping can in turn obey different models based on user preference, a default, etc. A first is a simple spring expansion model in which the displacement is shared equally starting from the fixed point to the loaded point. Another is a damped spring expansion model in which the displacement is more at a loaded point and gradually reduces towards a fixed point. The simple spring is well-suited for instances where the expected organ movement and/or deformation causes an equal and linear contraction or expansion in the nearest neighborhood as well as in the farthest regions from the deformed organ. The damped spring model is well-suited for instances where the expected expansion/contraction resulting from organ movement or deformation is greater in the nearest neighborhood and less farther from the organ.

Retuning to FIG. 2, an organ movement and/or deformation analyzer 206 processes the ROI in the warped image and generates dose distributions for the ROI movement and/or deformation.

The treatment planner 126 further receives, as input, a set of setup uncertainty such as an estimate of whole body movement of the patient in six directions (three pair of positive and negative coordinates), range uncertainty, etc.

A setup error analyzer 208 processes the setup error (range and setup uncertainty) and generates a dose distribution optimized for the setup error.

A robustness optimizer 210 processes the estimated nominal dose distribution, the dose distributions for the setup error, and the dose distributions for the ROI movement and/or deformation. EQUATION 2 provides an example RO optimization for computing a RO OBV that takes into account the ROI movement and/or deformation.

$$\text{RO OBV} = \text{Nominal Plan OBV} + \text{Setup Error OBV} + \text{Organ Movement OBV} + \text{Organ deformation OBV} \quad \text{EQUATION 2:}$$

where Organ movement OBV=(Organ A(+X error OBV)+(−X error OBV)+(+Y error OBV)+(−Y error OBV)+(+Z error OBV)+(−Z error OBV))+(Organ B(+X error OB)+(−X error OBV)+(+Y error OBV)+(−Y error OBV)+(+Z error OBV)+(−Z error OBV), and Organ deformation OBV=(Organ A(X contraction OBV)+(X elongation OBV)+(Y contraction OBV)+(Y elongation OBV)+(Z contraction OBV)+(Z elongation OBV)+(Organ B(X contraction OBV)+(X elongation OBV)+(Y contraction OBV)+(Y elongation OBV)+(Z contraction OBV)+(Z elongation OBV).

For Organ Movement OBV, each objective value represents a respective uncertainty scenario, e.g., Organ B (+X error OBV) is the objective value obtained from the dose statistics when the organ B is in displaced place by a factor specified by the user. For Organ deformation OBV, each objective value represents the respective uncertainty scenario, e.g., Organ A (X contraction OBV) is the objective value obtained from the dose statistics when the organ A is in contracted state. In a variation, the Organ Movement OBV component is omitted from EQUATION 2, and EQUATION 2 takes into account internal organ deformation but not internal organ movement. In yet another variation, the Organ deformation OBV component is omitted from EQUATION 2, and EQUATION 2 takes into account internal organ movement but not internal organ deformation.

The above describes an example using a composite objective value, which minimizes a summation of the difference objective components. In a variation, a voxel-wise, an objective-wise, and/or other optimization approach is employed.

A parameter and image combiner 212 combines the beam parameters obtained from using EQUATION 2 and the input image (i.e. the image without warping). This can be achieved by exporting the beam parameters obtained from the RO onto the input image. A dose distribution estimator 214 re-computes the dose distribution based thereon. This information is displayed via a display monitor, and a user can evaluate the treatment plan, e.g., to check the optimality of the dose distribution. The user, via an input device, can confirm, modify, re-compute, or reject the plan. An IMPT plan with an accepted dose distribution is provided to the console 122, which instructs the controller 124 based thereon for a proton beam therapy treatment.

Figure 7:
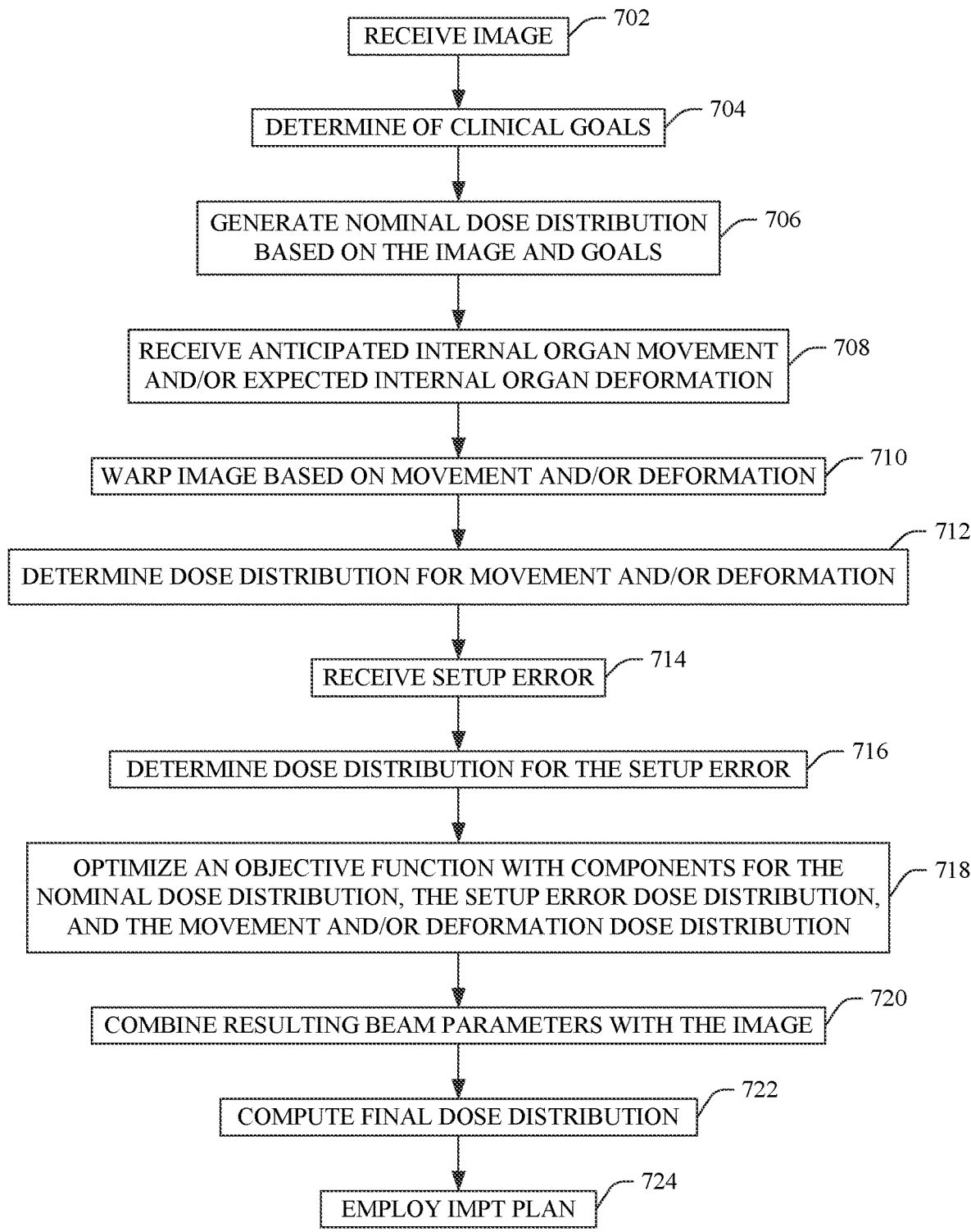
FIG. 7 illustrates an example method for optimized IMPT plan that takes into account internal organ movement and/or deformation.

FIG. 7 illustrates an example method for optimized IMPT plan that takes into account internal organ movement and/or deformation.

It is to be appreciated that the ordering of the acts in the methods described herein is not limiting. As such, other orderings are contemplated herein. In addition, one or more acts may be omitted and/or one or more additional acts may be included.

At 702, an image for creating an IMPT plan is received.

At 704, a set of clinical goals are determined.

At 706, a nominal dose distribution is generated for the image and the clinical goals.

At 708, anticipated internal organ movement and/or expected internal organ deformation information is received, as described herein and/or otherwise.

At 710, the image is warped based on the organ movement and/or deformation information, as described herein and/or otherwise.

At 712, a dose distribution for the movement and/or deformation is determined, as described herein and/or otherwise.

At 714, setup error is received.

At 716, a dose distribution for the setup error is determined.

At 718, an objective function including components for the nominal dose distribution, the dose distribution for the setup error, and the dose distribution for the movement and/or deformation is optimized, as described herein and/or otherwise.

At 720, the resulting beam parameters are combined with the image, as described herein and/or otherwise.

At 722, a final dose distribution is estimated based thereon, as described herein and/or otherwise.

At 724, the IMPT plan with the final dose distribution is employed by the system 100 to execute a proton treatment.

The following provides examples in connection with MR therapy. This includes deformation of MR images on treatment sites where there are more tissues than bones using algorithms to convert MR images to CT images on which radiation treatment planning is performed. This allows for improved deformation due at least to more tissues in the MR images relative to CT images.

Figure 8:
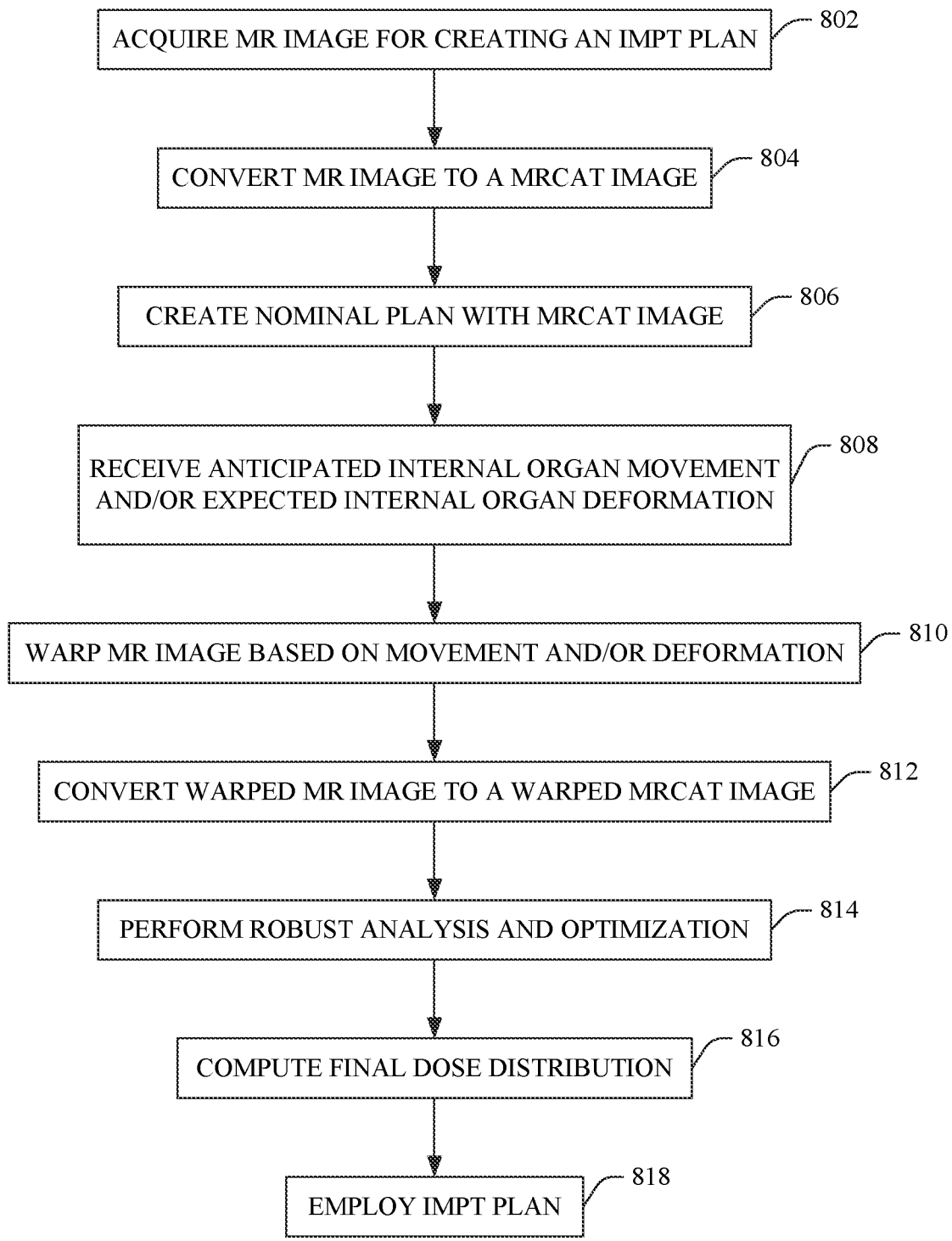
FIG. 8 illustrates an example method for MR therapy using only MR images.

FIG. 8 illustrates an example method for MR therapy. This method is fully MR-based (i.e., no additional radiation exposure due to CT acquisition) and leverages soft tissue contrast.

It is to be appreciated that the ordering of the acts in the methods described herein is not limiting. As such, other orderings are contemplated herein. In addition, one or more acts may be omitted and/or one or more additional acts may be included.

At 802, an MR imaging system is used to scan a subject and generate an MR image for creating an IMPT plan.

At 804, the MR image is converted into a pseudo CT image such as a MR for Calculating ATtenuation (MRCAT) image. Known and/or other algorithms can be employed to convert the MR images. Converting a CT image to a MRCAT image is discussed at http://www.philips.com.eg/healthcare/education-resources/publications/hotspot/prostate-rt-planning and in Kohler et al., "MR-only simulation for radiotherapy planning."

At 806, a nominal plan is created in the MRCAT image.

At 808, anticipated internal organ movement and/or expected internal organ deformation information is obtained, as described herein and/or otherwise.

At 810, the MR image is warped based on the organ movement and/or deformation producing a warped image, as described herein and/or otherwise.

At 812, the warped MR image is converted to a warped MRCAT image. Known and/or other algorithms can be employed to convert the deformed MR images.

At 814, a robustness analysis and optimization is performed, as described herein (e.g., acts 712-724 of FIG. 7) and/or otherwise.

At 816, a final dose distribution is estimated based thereon, as described herein and/or otherwise.

At 818, the IMPT plan with the final dose distribution is employed by the system 100 to execute a proton treatment.

Figure 9:
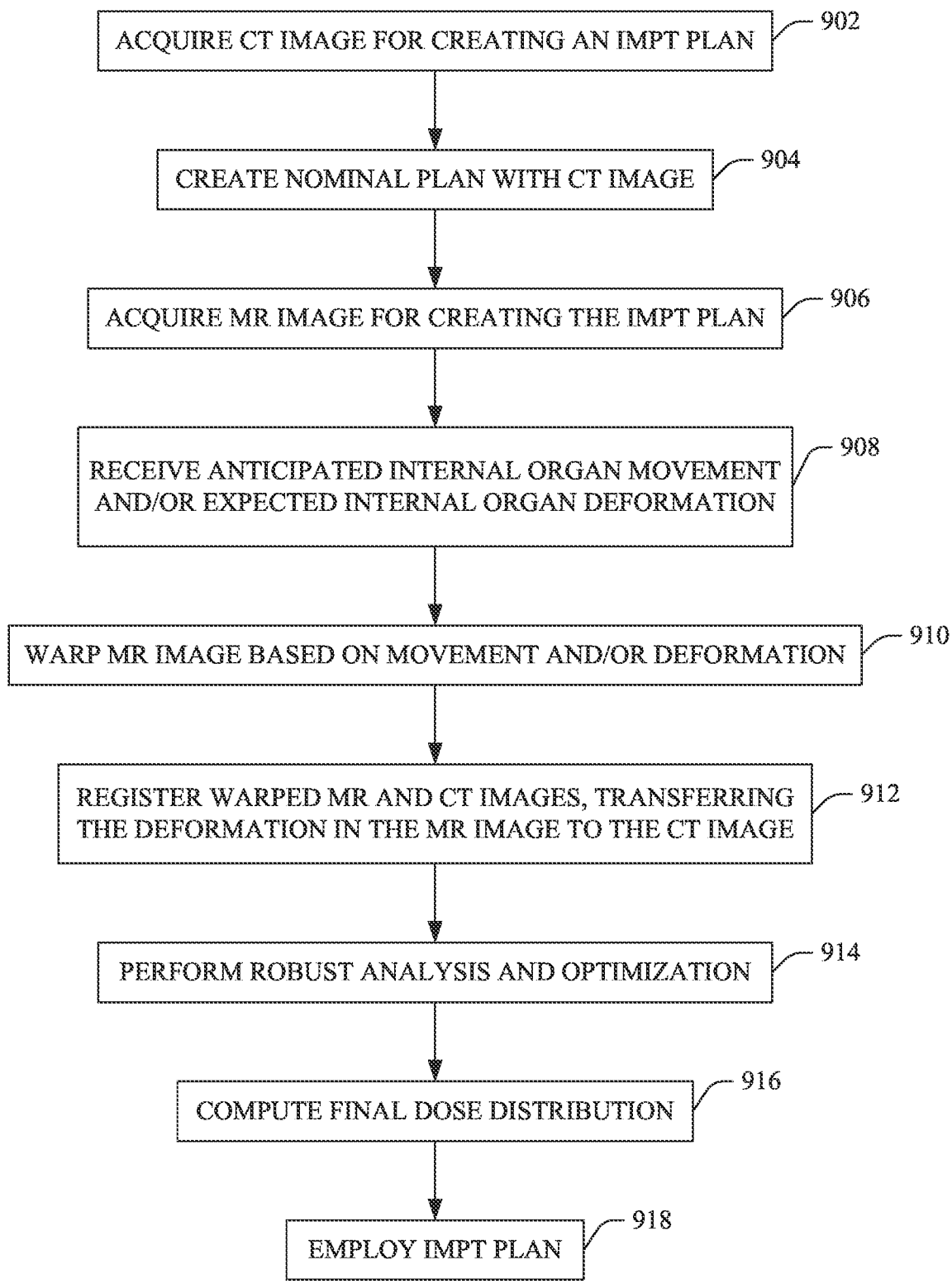
FIG. 9 illustrates an example method for MR therapy using CT and MR images.

FIG. 9 illustrates another example method for MR therapy. This method uses both a CT image and a MR image. A nominal plan is created using actual CT and thus is more accurate in terms of dose computation, and the soft tissue information from the MR image is incorporated in the process.

It is to be appreciated that the ordering of the acts in the methods described herein is not limiting. As such, other orderings are contemplated herein. In addition, one or more acts may be omitted and/or one or more additional acts may be included.

At 902, an CT imaging system is used to scan a subject and generate a CT image for creating an IMPT plan.

At 904, a nominal plan is created.

At 906, an MR imaging system is used to scan a subject and generate an MR image for creating an IMPT plan.

At 908, anticipated internal organ movement and/or expected internal organ deformation information is obtained, as described herein and/or otherwise.

At 910, the MR image is warped based on the organ movement and/or deformation producing a warped MR image, as described herein and/or otherwise.

At 912, a deformable image registration (e.g., MR to CT fusion, etc.) is applied between the CT and warped MR, which transfers the deformations in MR image to the CT image.

At 914, a robustness analysis and optimization is performed, as described herein (e.g., acts 712-724 of FIG. 7) and/or otherwise.

At 916, a final dose distribution is estimated based thereon, as described herein and/or otherwise.

At 918, the IMPT plan with the final dose distribution is employed by the system 100 to execute a proton treatment. Optionally, the estimate may be subject to a validation step by a validation system.

The methods herein may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
generating a nominal dose distribution based on an image and clinical goals;
generating a setup error dose distribution based on range and setup uncertainties;
warping the image based on a parameter of an internal organ to produce a warped image;
generating a dose distribution for the parameter of the internal organ with the warped image;
optimizing a planned dose distribution of an intensity modulated proton therapy plan by minimizing a total objective value including the nominal dose distribution, the setup error dose distribution, and the dose distribution for the internal organ;
generating a final dose distribution for the intensity modulated proton therapy plan based on beam parameters of the optimized planned dose distribution; and
controlling a proton therapy apparatus to deliver proton therapy based on the intensity modulated proton therapy plan with the optimized planned dose distribution.

2. The method of claim 1, wherein the parameter of the internal organ includes anticipated internal organ movement.

3. The method of claim 2, wherein the anticipated internal organ movement includes movement in three-dimensions.

4. The method of claim 1, wherein the parameter of the internal organ includes expected internal organ deformation.

5. The method of claim 4, wherein the expected internal organ deformation includes deformation in three-dimensions.

6. The method of claim 1, wherein warping the image comprises:
determining a deformation vector field for the parameter of the internal organ; and
applying the deformation vector field to the image.

7. The method of claim 6, wherein warping the image includes warping only a sub-region of interest of the internal organ.

8. The method of claim 7, wherein the deformation vector field is applied to an external contour of the sub-region of interest of the internal organ.

9. The method of claim 7, wherein the deformation vector field is applied to a region contained in the sub-region of interest of the internal organ.

10. The method of claim 7, wherein the deformation vector field is applied to a pre-determined region about the sub-region of interest of the internal organ.

11. The method of claim 10, wherein warping the image is based on an elastic expansion-contraction model in which the pre-determined region expands in response to the sub-region of interest contracting, and the pre-determined region contracts in response to the sub-region of interest expanding.

12. The method of claim 11, wherein the elastic expansion-contraction model is at least one of a simple spring expansion model in which displacement is shared equally or a damped spring expansion model in which the displacement is unequal.

13. A system comprising:
a treatment planner including a processor configured to generate an optimized intensity modulated proton therapy plan based on an input image, a nominal dose distribution, a setup error dose distribution, and a dose distribution for at least one of an internal organ movement or an internal organ deformation, wherein the treatment planner comprises:

a robustness optimizer configured to optimize a planned dose distribution of an intensity modulated proton therapy plan by minimizing a total objective value including the nominal dose distribution, the setup error dose distribution, and the dose distribution for the at least one of the internal organ movement or the internal organ deformation, producing optimized beam parameters.

14. The system of claim 13, wherein the treatment planner further comprises:
an image warper configured to warp the input image, based on an anticipated movement of an internal organ and an expected deformation of the internal organ, producing a warped image; and
an organ movement and/or deformation analyzer configured to process the warped image and compute the dose distribution for the at least one of the internal organ movement or the internal organ deformation.

15. The system of claim 13, wherein the treatment planner further comprises:
a parameter and image combiner configured to export the beam parameters to the input image.

16. The system of claim 15, wherein the treatment planner further comprises:
a dose distribution estimator configured to compute a final dose distribution for the optimized intensity modulated proton therapy plan based on the exported beam parameters.

17. The system of claim 13, further comprising:
a proton therapy apparatus configured to deliver proton therapy;
a controller configured to control the proton therapy apparatus; and
a console configured to instruct the controller to control the proton therapy apparatus to transmit a proton beam based on the optimized intensity modulated proton therapy plan.

18. A non-transitory computer readable medium encoded with computer executable instructions, which when executed by a processor, causes the processor to:
receive an image;
receive a first input indicative of a nominal dose distribution for the received image and clinical goals;
receive a second input indicative of a setup error dose distribution for range and setup uncertainties;
receive a third input indicative of an anticipated movement of an internal organ;
receive a fourth input indicative of an expected deformation of the internal organ;
warp the received image based on the anticipated movement and the expected deformation, generating a warped image;
compute a dose distribution for the warped image;
optimize a planned dose distribution of an intensity modulated proton therapy based on the nominal dose distribution, the setup error dose distribution, and the dose distribution for the anticipated movement and the expected deformation;
export beam parameters obtained from the optimized planned dose distribution to the received image; and
generate a final dose distribution for the intensity modulated proton therapy based on the exported beam parameters.

19. The non-transitory computer readable medium of claim 18, wherein the computer executable instructions cause the processor to warp the received image by:
determining a deformation vector field for the anticipated movement of the internal organ; and
applying the deformation vector field to the received image.

20. The non-transitory computer readable medium of claim 19, wherein only a sub-region of interest of the internal organ is warped, and
wherein the deformation vector field is applied to a pre-determined region about the sub-region of interest of the internal organ.

21. The non-transitory computer readable medium of claim 20, wherein the received image is warped based on an elastic expansion-contraction model in which the pre-determined region expands in response to the sub-region of interest contracting, and the pre-determined region contracts in response to the sub-region of interest expanding.

* * * * *